(12) United States Patent
Martinez Ferreira

(10) Patent No.: US 12,290,396 B2
(45) Date of Patent: May 6, 2025

(54) CABLE MANAGEMENT CLAMP AND METHOD FOR SECURING CABLES IN C-ARM IMAGING SYSTEMS

(71) Applicant: GE Precision Healthcare LLC, Wauwatosa, WI (US)

(72) Inventor: Carlos Martinez Ferreira, Paris (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 298 days.

(21) Appl. No.: 17/977,165

(22) Filed: Oct. 31, 2022

(65) Prior Publication Data

US 2024/0138802 A1 May 2, 2024

(51) Int. Cl.
*A61B 6/00* (2024.01)

(52) U.S. Cl.
CPC .............. *A61B 6/56* (2013.01); *A61B 6/4441* (2013.01)

(58) Field of Classification Search
CPC ........... A61B 6/56; A61B 6/4441; A61B 6/44; A61B 6/4417; A61B 6/4429; A61B 6/54; H02G 11/006; F16G 13/16
See application file for complete search history.

(56) References Cited

U.S. PATENT DOCUMENTS

| | | | | |
|---|---|---|---|---|
| 4,059,871 A | * | 11/1977 | Swager | E06C 7/186 |
| | | | | 182/8 |
| 5,692,984 A | * | 12/1997 | Kayatani | B23Q 5/34 |
| | | | | 483/68 |
| 6,387,002 B1 | | 5/2002 | Gunter | |
| 6,491,430 B1 | * | 12/2002 | Seissler | A61B 6/466 |
| | | | | 378/207 |
| 10,378,610 B2 | | 8/2019 | Jaeker | |
| 2002/0017428 A1 | * | 2/2002 | Mauthner | A62B 1/14 |
| | | | | 182/5 |

(Continued)

FOREIGN PATENT DOCUMENTS

DE 202017104900 U1 11/2018
EP 2546546 B1 10/2015

OTHER PUBLICATIONS

DE202017104900 English Translation Abstract; Espacenet.com search Aug. 22, 2024; 1 page.

(Continued)

*Primary Examiner* — David P Porta
*Assistant Examiner* — Gisselle M Gutierrez
(74) *Attorney, Agent, or Firm* — Boyle Frederickson, S.C

(57) ABSTRACT

A clamp for releasably engaging a cable chain employed on a C-arm X-ray imaging device includes a positioning member having a rear surface formed complementary to a portion of the C-arm imaging device, a pivot arm attached to the positioning member, a biasing member disposed on the pivot arm, and a clamp arm rotatably mounted to the pivot arm, wherein the biasing member is engaged between the positioning member and the clamp arm to move the clamp arm between a release position and a locking position. The clamp is engageable with the cable chain to hold the cable chain in alignment with the at least one of the housing and the C-arm, and is operable separately from the imaging device, such that the clamp can hold the cable chain on the housing or C-arm even when power is not provided to the imaging device.

18 Claims, 10 Drawing Sheets

(56) References Cited

U.S. PATENT DOCUMENTS

| | | | |
|---|---|---|---|
| 2012/0121071 A1* | 5/2012 | Herrmann | A61B 6/4441 |
| | | | 378/194 |
| 2015/0211658 A1* | 7/2015 | Lu | F16G 13/16 |
| | | | 59/78.1 |
| 2019/0029620 A1* | 1/2019 | Baumann | B25J 19/0025 |
| 2019/0329665 A1* | 10/2019 | Curran | B60L 53/12 |
| 2021/0085264 A1 | 3/2021 | Cleary | |
| 2021/0145384 A1* | 5/2021 | Daugirdas | A61B 6/4441 |
| 2023/0284987 A1* | 9/2023 | Cleary | A61B 6/56 |
| 2024/0138789 A1* | 5/2024 | Martinez Ferreira | |
| | | | A61B 6/4441 |
| 2024/0138802 A1* | 5/2024 | Martinez Ferreira | A61B 6/56 |

OTHER PUBLICATIONS

EP 2546546 English Translation Abstract; Espacenet.com search Aug. 22, 2024; 1 page.
EP application 23202820.9 filed Oct. 10, 2023—extended Search Report issued May 24, 2024; 13 pages.

\* cited by examiner

CABLE MANAGEMENT CLAMP AND METHOD FOR SECURING CABLES IN C-ARM IMAGING SYSTEMS

BACKGROUND OF DISCLOSURE

The subject matter disclosed herein relates to X-ray imaging systems having C-arms and, more particularly, to cable management systems to maintain power, cooling and control cables in alignment with the C-arm throughout motion of the C-arm along multiple independent rotational axes.

Medical diagnostic imaging systems generate images of an object, such as a patient, for example, through exposure to an energy source, such as X-rays passing through a patient, for example. The generated images may be used for many purposes. Often, when a practitioner takes X-rays of a patient, it is desirable to take several X-rays of one or more portions of the patient's body from a number of different positions and angles, and preferably without needing to frequently reposition the patient. To meet this need, C-arm X-ray diagnostic equipment has been developed. The term C-arm generally refers to an X-ray imaging device having a rigid and/or articulating structural member having an X-ray source and an image detector assembly that are each located at an opposing end of the structural member so that the X-ray source and the image detector face each other. The structural member is typically "C" shaped and so is referred to as a C-arm. In this manner, X-rays emitted from the X-ray source can impinge on the image detector and provide an X-ray image of the object or objects that are placed between the X-ray source and the image detector.

In many cases, C-arms are connected to one end of a movable arm disposed on a base or gantry. In such cases, the C-arm can often be raised and lowered, be moved from side to side, and/or be rotated about one or more axes of rotation via the moveable arm. Accordingly, such C-arms can be moved and reoriented to allow X-ray images to be taken from several different positions and angles and different portions of a patient, without requiring the patient to be frequently repositioned.

However, rotation or motion of the C-arm may be limited in certain directions (e.g., orbital direction) due to the structure of the imaging system. In particular, the C-am includes a number of cables/cabling connected between the base and the C-arm for supplying power, control signals and data to and from the X-ray source and detector. AS shown in FIG. 1, the cables extend outwardly from the base and are connected to the exterior of the C-arm and must each have a length sufficient to accommodate all degrees and ranges of motion of the C-arm in relation to the base, while also being formed in a suitable manner to perform the specified functions, e.g., stiff cables for high voltage power transmission or directing flows of a cooling fluid.

The number, length and stiffness of the cables necessary for the operation of the C-arm and X-ray source and detector disposed thereon can create obstructions to visibility and/or access in areas around the C-arm and the base during movement of the due to the cabling looping into these areas based on the position of the C-arm relative to the base. Further, with regard to the fast movement of the C-arm between different imaging orientations, the cables can become separated from the structure of the C-arm to create an obstruction, particularly in situations where the C-ram is an extended position relative to the gantry or base.

To assist in holding the cables where desired on the C-arm and imaging device, a number of different types of clamping mechanisms/clamps have been developed. These clamps can be disposed on the C-arm and engage the cables in a manner that holds the cables on the C-arm. The clamps take various forms and include magnetic mechanisms and spring-biased or pusher mechanisms that engage and hold the cables on the C-arm. However, these types of clams are not self-locking and can readily become disengaged from the cables upon application of a sufficient force to the clamp, such as the force of the generated on the cables through the movement of the C-arm during normal operation of the imaging device.

Other types of clamps are deigned to be self-locking to more securely hold the cables in the desired positions on the C-arm. For example, certain types of cable chains are designed to retain the cables inserted therein and to engage complementary structures on the C-arm to lock the cable chain, and the cables positioned within the cable chain, in position on the C-arm. However, while these self-locking clamps can securely hold the cable chain and cables in the desired positions on the C-arm, the construction of the cable chain and complementary securing structures are highly specific to one another, allowing only for the use of cable chains with only complementary structures.

Therefore, it is desirable to develop a cable management clamp and method for securing the cables for the imaging system on the C-ram in a manner that provides a self-locking system without the need for specialized cable management equipment and/or chains, and that maintains the cables in a desired position relative to the C-arm to minimize obstructions in the area around the C-arm and maximize the area available for use by medical practitioners and/or other medical devices for patient treatment.

BRIEF DESCRIPTION OF THE DISCLOSURE

According to one exemplary non-limiting aspect of the disclosure, a C-arm x-ray imaging device includes a base, a carriage operably connected to the base and having at least one axis of movement with respect to the base; a C-arm movably connected to the carriage, the C-arm including an x-ray source and an x-ray detector disposed thereon in alignment with one another and a cable management system having a housing disposed on the carriage, the housing defining an interior, a number of cables extending from the base into the interior of the housing, a cable chain having a first end secured within the interior of the housing and a second end affixed to the C-arm, the cable chain defining a channel therein that receives the number of cables to direct the number of cables from the base to the C-arm, and at least one clamp releasably engageable with the cable chain to hold the cable chain in alignment with the at least one of the housing and the C-arm.

According to still another aspect of one exemplary non-limiting embodiment of the disclosure, a clamp for releasably engaging a cable chain employed on a C-arm X-ray imaging device includes a positioning member having a rear surface formed complementary to a portion of the C-arm imaging device, a pivot arm attached to the positioning member, a biasing member disposed on the pivot arm, and a clamp arm rotatably mounted to the pivot arm, wherein the biasing member is engaged between the positioning member and the clamp arm to move the clamp arm between a release position and a locking position.

According to still another aspect of one exemplary non-limiting embodiment of the disclosure, a method of managing the position of cables connecting a detector and an x-ray source of a C-arm to a base of a C-arm x-ray imaging device includes the steps of providing a C-arm-ray imaging device having a base, a carriage operably connected to the base and having at least one axis of movement with respect to the base, a C-arm movably connected to the carriage, the C-arm including an x-ray source and an x-ray detector disposed thereon in alignment with one another, and a cable management system including a housing disposed on the carriage, the housing defining an interior, a number of cables extending from the base into the interior of the housing, a cable chain having a first end secured within the interior of the housing and a second end affixed to the C-arm, the cable chain defining a channel therein that receives the number of cables to direct the number of cables from the base to the C-arm, and at least one clamp releasably engageable with the cable chain to hold the cable chain in alignment with the at least one of the housing and the C-arm, placing the number of cables within the cable chain, moving the C-arm relative to the carriage and engaging the cable chain with the at least one clamp to maintain the cable chain within a profile of at least one of the housing or the C-arm.

It should be understood that the brief description above is provided to introduce in simplified form a selection of concepts that are further described in the detailed description.

BRIEF DESCRIPTION OF THE DRAWINGS

The drawings illustrate the best mode presently contemplated of carrying out the disclosure. In the drawings.

DETAILED DESCRIPTION

Figure 1:
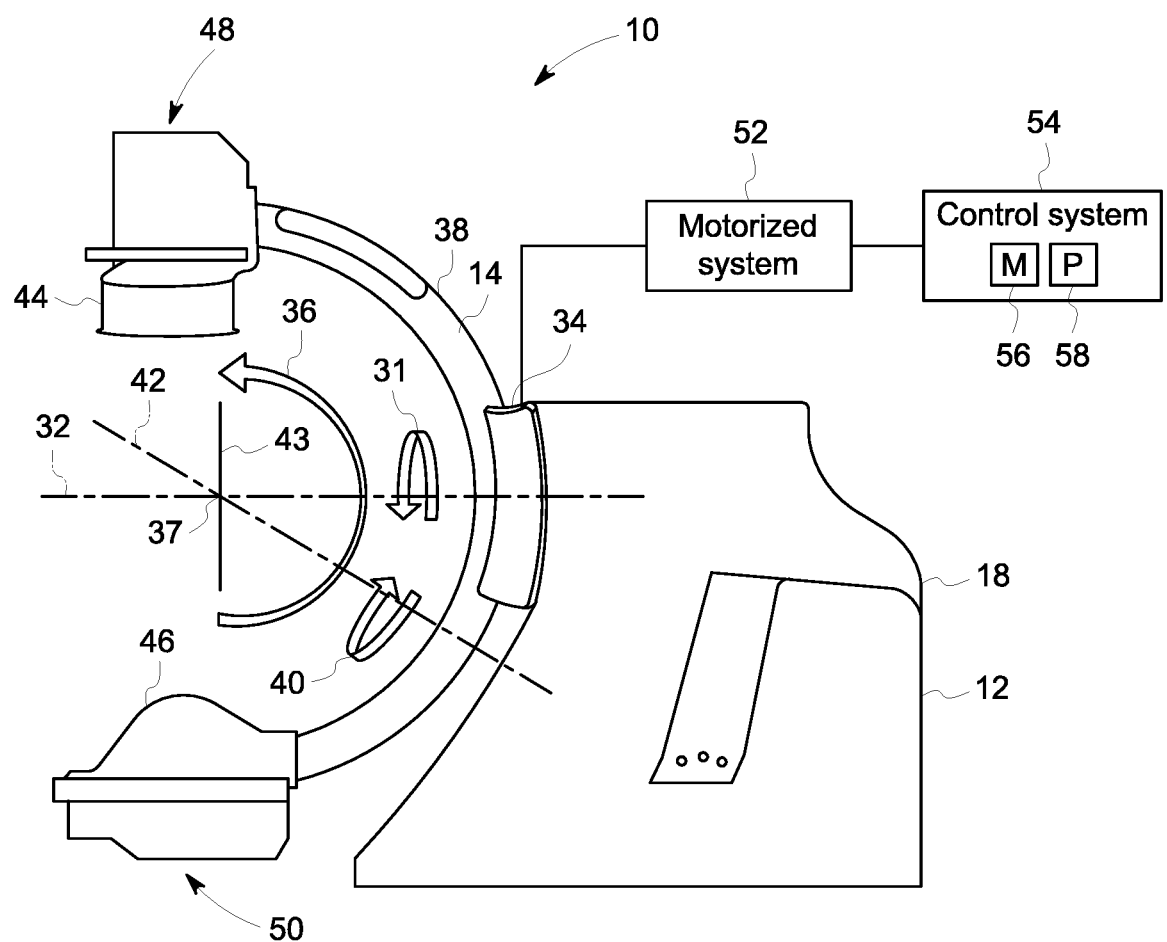
FIG. 1 is a side elevation view of an embodiment of prior art C-arm imaging system having multiple independent rotational axes.
Figure 2:
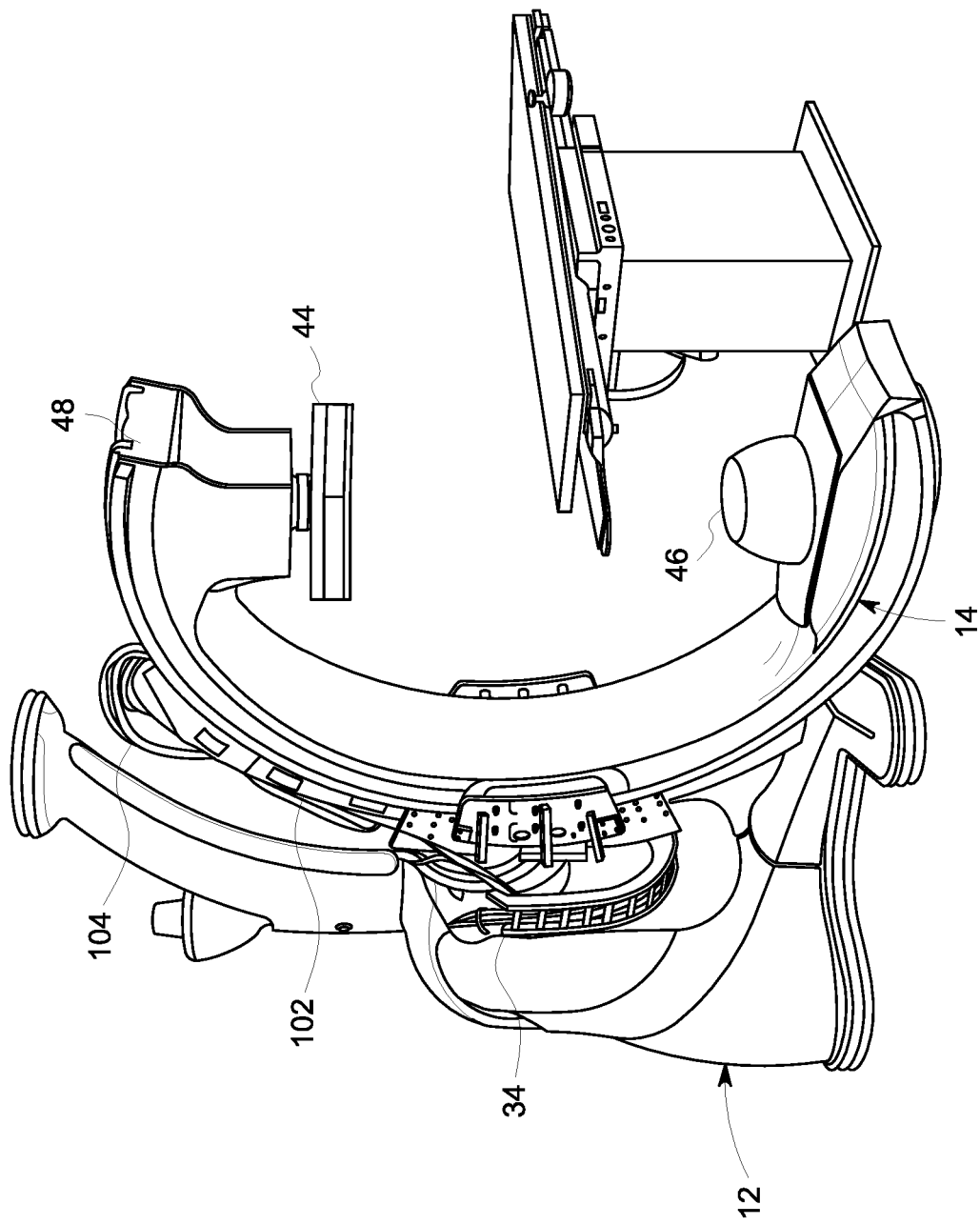
FIG. 2 is a side elevation view of an embodiment of a C-arm imaging system having multiple independent rotational axes according to one exemplary non-limiting embodiment of the invention.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The following embodiments describe an X-ray imaging system (e.g., fixed X-ray imaging system) having automated C-arm motion about multiple independent (e.g., separate or different) rotational axes (e.g., 3 or more). For example, the C-arm may rotate about 3 different axes: a lateral axis, an orbital axis, and a flip-flop axis (e.g., defined by rotation about where the C-arm is coupled to an L-arm). The motion about these 3 different axes may be automated (e.g., via a motorized system including multiple motors or servomotors). The automated motion about these 3 different axes may increase the orbital range or coverage with the C-arm in the orbital direction without having to move the patient and/or table the patient is disposed on. Motorization of all of these axes (especially the flip-flop axis) provides numerous advantages. For example, motorized motion compared to manual motion may be controlled remotely to reduce radiation exposure. In addition, motorization of all these axes enables the capture of image data for three-dimensional (3D) image generation in the orbital direction, while still allowing the X-ray imaging system to be utilized as a general purpose C-arm imaging system. Typically, increasing the orbital motion about a single axis keeps the imaging system from being utilized in general procedures (e.g., procedures in orthopedics, gastroenterology, cardiology, etc.). However by automating all of these axes, a general purpose C-arm imaging system may also be utilized as an accurate 3D image capturing imaging system.

FIG. 1 is a side view of an embodiment of an X-ray imaging system 10 (e.g., a fixed C-arm imaging system) having multiple independent rotational axes. Although a mobile imaging system is illustrated, the embodiments described below may be utilized with any X-ray imaging system having a C-arm (e.g., a mobile C-arm imaging system). The X-ray imaging system 10 may utilize multiple imaging modalities (e.g., fluoroscopy, computed tomography, tomosynthesis, radiographic, magnetic resonance imaging, etc.) to acquire two-dimensional 2D and/or 3D image data. The X-ray imaging system 10 may be utilized for both diagnostic and interventional imaging. In addition, the X-ray imaging system 10 may be utilized for general purposes (e.g., general radiology, orthopedics, etc.) and special purposes (e.g., image guided surgery).

A principal function of the mobile X-ray imaging system 10 is to generate X-rays for diagnostic and interventional imaging. The X-ray imaging system 10 includes a support structure or base 12, a C-arm 14 connected to the base or gantry 12 via a carriage 34, and a control panel 18. The base 12 provides support for the C-arm 14 and holds the C-arm 14 in a suspended position. The base 12 includes a vertical lift column (not shown) operably connected to the carriage 34 that permits the C-arm 14 and carriage 34 to move vertically in relation to base 12. Vertical lift column can optionally include a horizontal extension arm (not shown) operably connected to the carriage 34 and the vertical lift column that permits the C-arm 14 to move perpendicularly in relation to vertical lift column by movement (e.g., horizontal movement) of the horizontal extension arm in relation to the base 12. The C-arm 14 may be moved along the axis of the horizontal extension arm to effect transverse tracking motion. The carriage 34 is optionally coupled to the horizontal extension arm/base 12 and configured to pivot or rotate about the horizontal extension arm such that the C-arm 14 can be made to pivot in a 360 degree arc in a lateral direction 31 (e.g., circumferential direction) about a lateral axis 32 (e.g., parallel to the horizontal extension arm) relative to the base 12.

The C-arm 14 is coupled to a C-arm rotation device 34 (e.g., carriage) that is coupled to the base 12. The C-arm rotation device/carriage 34 is coupled to an assembly of rollers or wheels (e.g., disposed within a track 38 of the C-arm 14) that enables the C-arm 14 to be directed, move or rotate about an orbital axis 37 (e.g., extending into and out of the page where axes 32, 42 intersect) in an orbital direction 36 along the track 38 relative to C-arm rotation device 34. As described in greater detail below, the X-ray imaging system 10 is configured to enable the C-arm 14 to rotate in the orbital direction 36 to provide an orbital range or coverage of at least 180 degrees relative to a location where the C-arm 14 is coupled to the base 12 (i.e., the C-arm rotation device 34).

The C-arm rotation device 34 also enables the C-arm 14 to rotate (e.g., circumferentially) or flip-flop (e.g., as indicated by reference numeral 40) about a flip-flop axis 42 (e.g., flip-flop axis) emanating from where the C-arm rotation device 34 is coupled to the C-arm 14 and, thus, the base 12. The C-arm rotation device 34 enables 180 degrees of rotation of the C-arm 14 relative to the C-arm rotation device 34.

Rotation of the C-arm 14 180 degrees (thereby enabling rotation about the lateral axis 32 and the flip-flop axis 42) enables the image chain to rotate 180 degrees about the orbital axis 37. An orbital plane 43 extends perpendicular to the orbital axis 37 and includes the image chain and the C-arm 14. The beginning orientation and the final orientation of the orbital plane 43 remains the same when the C-arm 14 is rotated about the lateral axis 32. However, during movement of the C-arm 14, the orbital plane 43 changes with the largest angular change occurring when the C-arm 14 is rotated 90 degrees.

An image receptor 44 (e.g., X-ray detector) and an X-ray source 46 are coupled to opposing ends 48, 50 of the C-arm 14 to form an image chain. The C-arm 14 allows the image receptor 44 and the X-ray source 46 to be mounted and positioned about an object to be imaged, such as a patient. The C-arm 14 may be a circular C-shaped or an arc-shaped member, for example. The C-arm 14 enables selective positioning of the image receptor/detector 44 and the X-ray source 46 with respect to the width and length of the patient or other object located within the interior free space of the C-arm 14. The image receptor/detector 44 may be an image intensifier or other energy receptor for using in diagnostic imaging, for example. The image receptor/detector 44 and the X-ray source 46 are used to generate a diagnostic image representative of the object being imaged.

Rotation about the axes 32, 37, and 42 are independent (e.g., separate or different from each other). Rotation of the C-arm 14 with respect to these axes 32, 37, 42 is driven by a motorized system 52. The motorized system 52 may include one or more motors or servomotors to drive the rotation about these axes 32, 37, 42 via automation. The motors or servomotors may be disposed throughout different components of the X-ray imaging system 10 (e.g., the upper housing of base 12, the C-arm rotation device 34, the C-arm 14, etc.). The motorized system 52 may be coupled to control system or controller 54 (e.g., disposed within the base 12 and/or remote from the X-ray imaging system 10). The control system 54 may include a memory 56 and one or more processors 58 to execute code or instructions stored within the memory 56. The control system 52 may control the automated movement of the C-arm 14 about the axes 32, 37, 42.

The automated or motorized movement of the C-arm 14 about the independent axes 32, 37, 42 increases the orbital range or coverage about the orbital axis 37 (i.e., allows the C-arm 14 to be rotated 180 degrees in the orbital direction 36). In particular, the orbital range may be increased to 180 degrees or greater. In particular, orbital rotation of the C-arm 14 180 degrees is achieved by rotating the C-arm 14 180 degrees about the lateral axis 32 and 180 degrees about the flip-flop axis 42.

Looking now at FIGS. 2-6, the imaging system 10 can include a cable management system 100 formed in part of a housing 102 disposed on and extending outwardly from one or both sides of the carriage 34. In the illustrated exemplary embodiment, the housing 102 is formed with a shape 102 that conforms to the shape of the C-arm 14 when a portion of the C-arm 14 is disposed adjacent the housing 102. A number of cables 104 extending from the base 12 and/or carriage 34 are positioned along an exterior 106 of the housing 102 opposite the C-arm 14 and around an end 108 of the housing 102 opposite the base 12/carriage 34 into an interior 110 of the housing 102. The cables 104 are secured to the exterior 106 of the housing 102 in any suitable manner (e.g., by mechanical fasteners) in order to maintain the position of the cables 104 relative to the housing 102 and carriage 34 when the carriage 34 and enclosure 34 are rotated with respect to the base 12 during the operation of the imaging system 10.

Within the interior 110 of the housing 102, the cables 104 are positioned within a cable chain 112 in order to maintain the order and alignment of the cables 104 with regard to the C-arm 14 during operation of the imaging system 10. The cable chain 112 is formed of a number of interconnected, articulating sections 114 that each define a channel 116 therein to receive the cables 104. The sections 114 each have a pair of side walls 118,120 pivotally joined to side walls 118,120 of adjacent sections 114, and pair of enclosure walls 122,124 extending between the side walls 118,120 to define the channel 116 therein. The pivoting connection of the sections 114 to one another allows the cable chain 112 to curve and maintain the alignment of the cable chain 112 with the C-arm 14.

One end 126 of the cable chain 112 is affixed to the housing 102 within the interior 110 adjacent the end 108. In this position the cables 104 can be directly inserted within the cable chain 112 in any suitable manner and routed through the cable chain 112. Opposite the end 108 of the housing 102, the other, second end 129 of the cable chain 112 is connected to the C-arm 14 at a location/connection point 128, e.g., adjacent the detector 44, where the cables 104 can be routed along and/or within the C-arm 14 for direct or other operable connection to the detector 44 and/or to the X-ray source 46.

Figure 3:
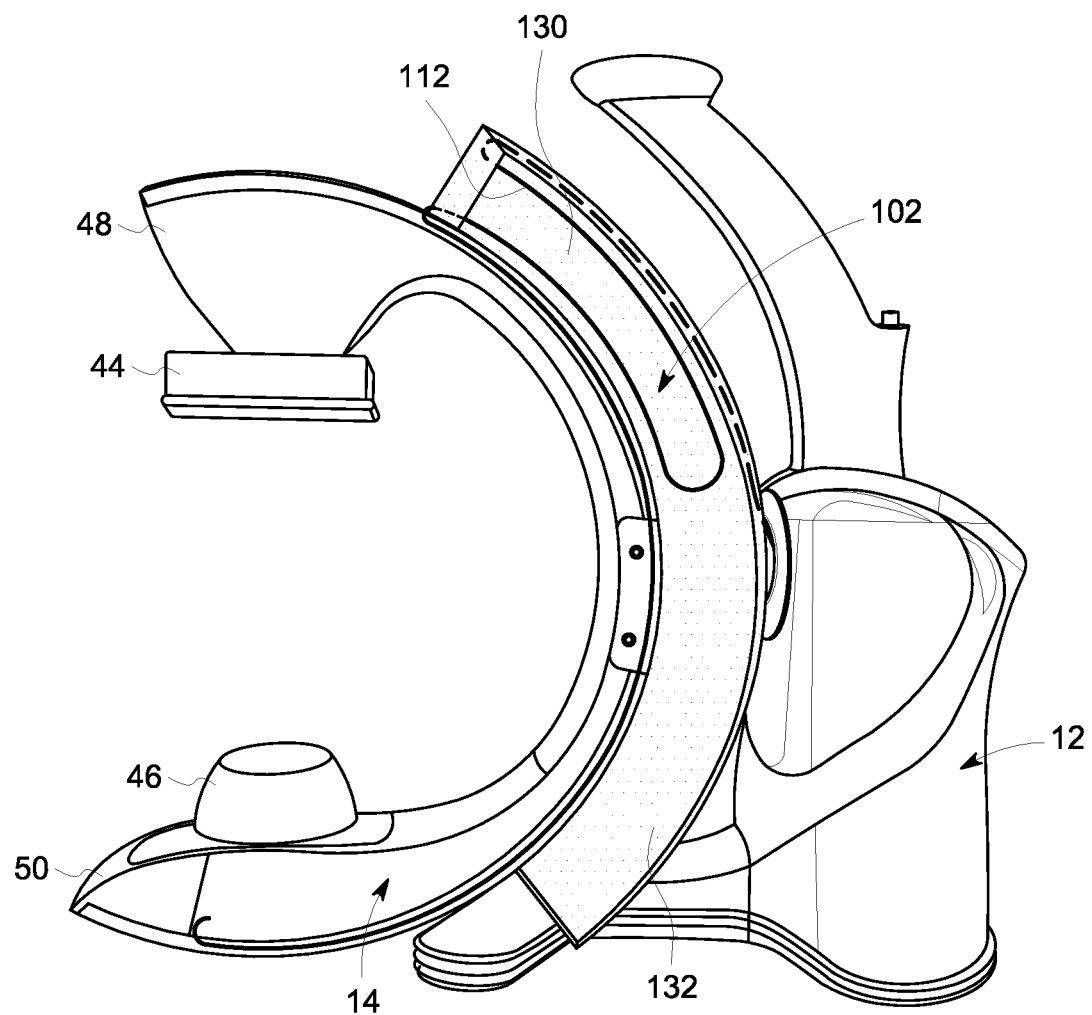
FIG. 3 is a partially broken away, side elevational view of the C-arm imaging system of FIG. 2 with the detector a vertical position.
Figure 4:
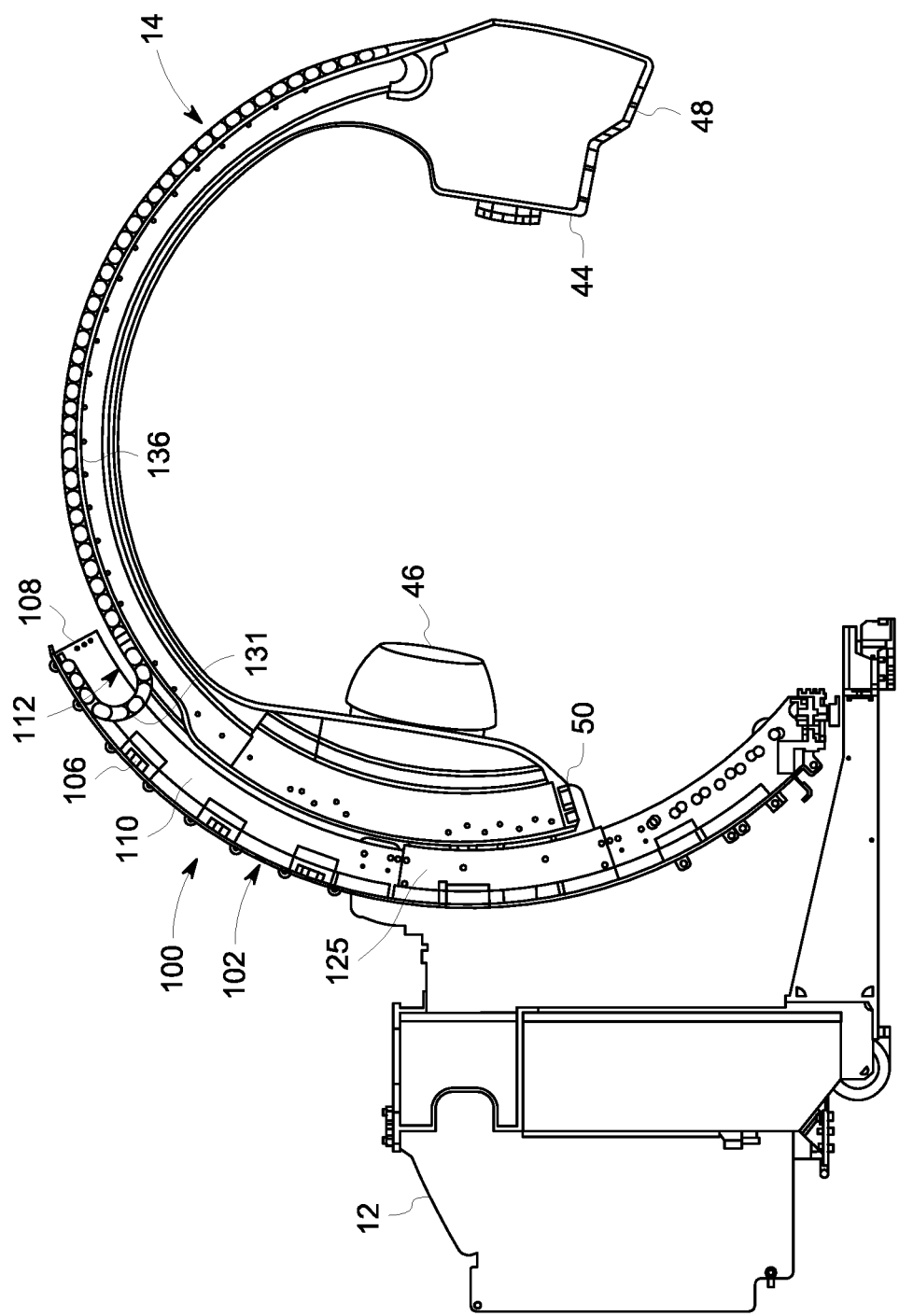
FIG. 4 is a partially broken away, side elevational view of the C-arm imaging system of FIG. 2 with the detector rotated +105 degrees relative to the position of FIG. 3.
Figure 5:
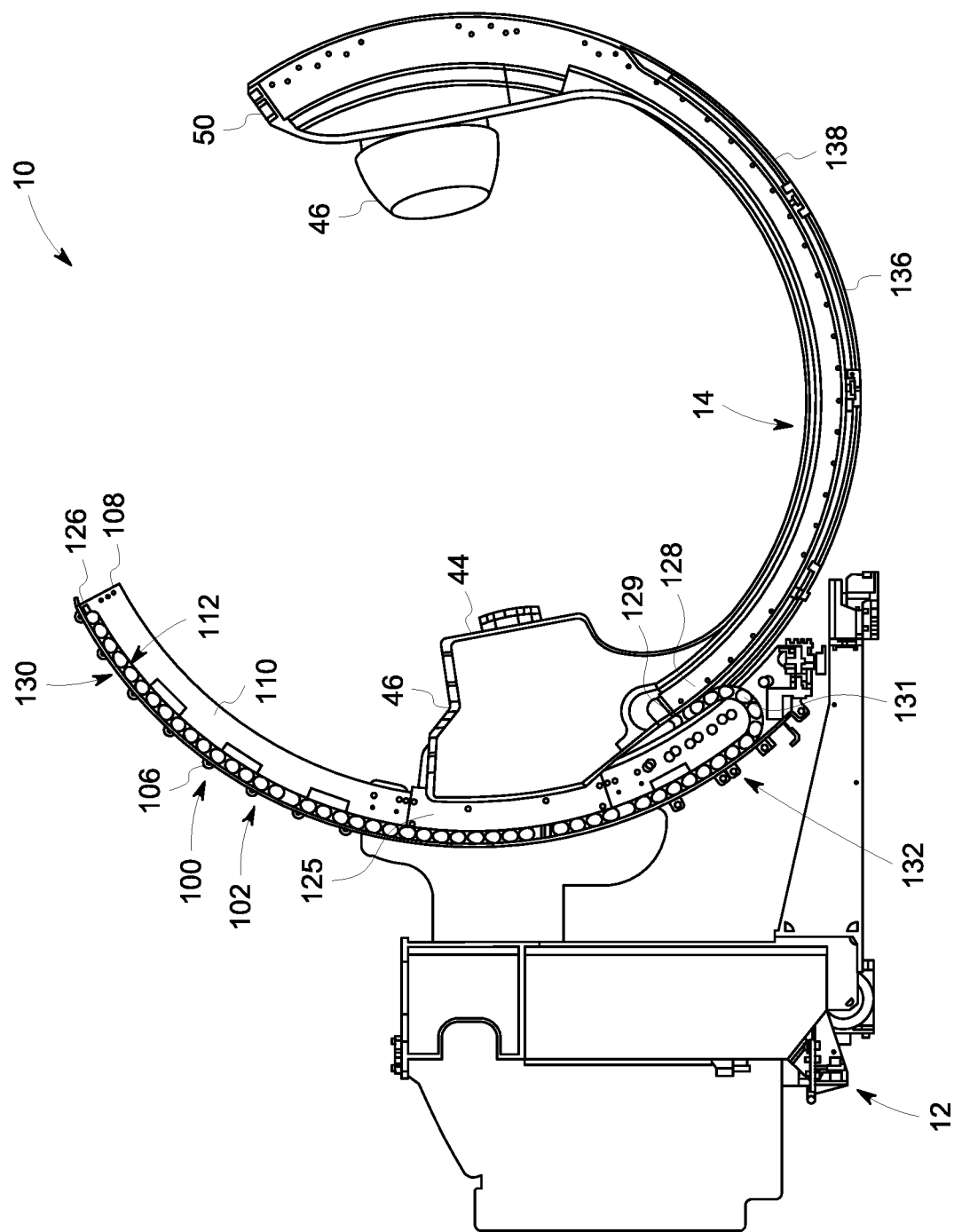
FIG. 5 is a partially broken away, side elevational view of the C-arm imaging system of FIG. 2 with the detector rotated −105 degrees relative to the position of FIG. 3.
Figure 6:
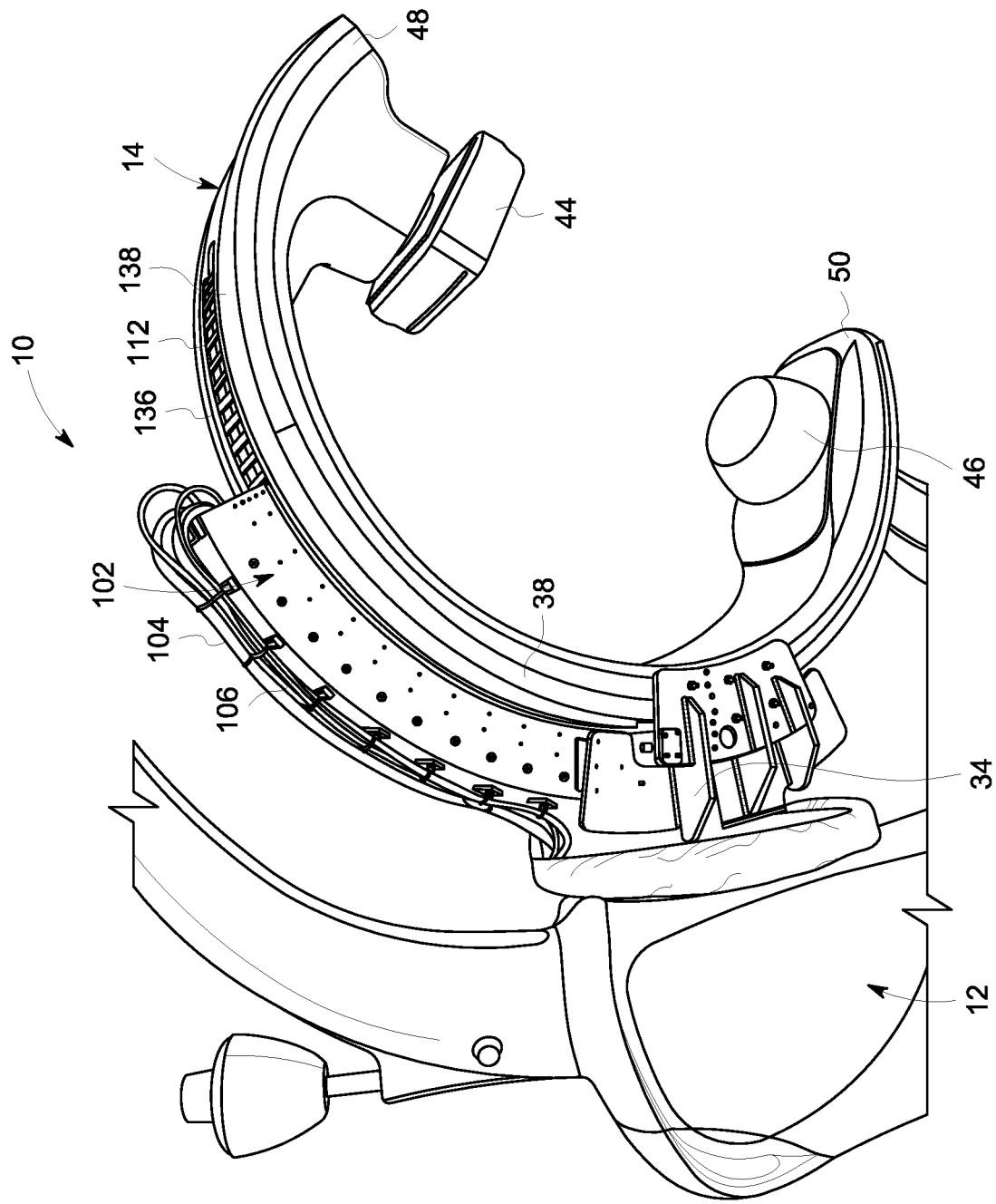
FIG. 6 is an isometric side view of the C-arm imaging system of FIG. 2 according to another exemplary embodiment of the disclosure.
Figure 7:
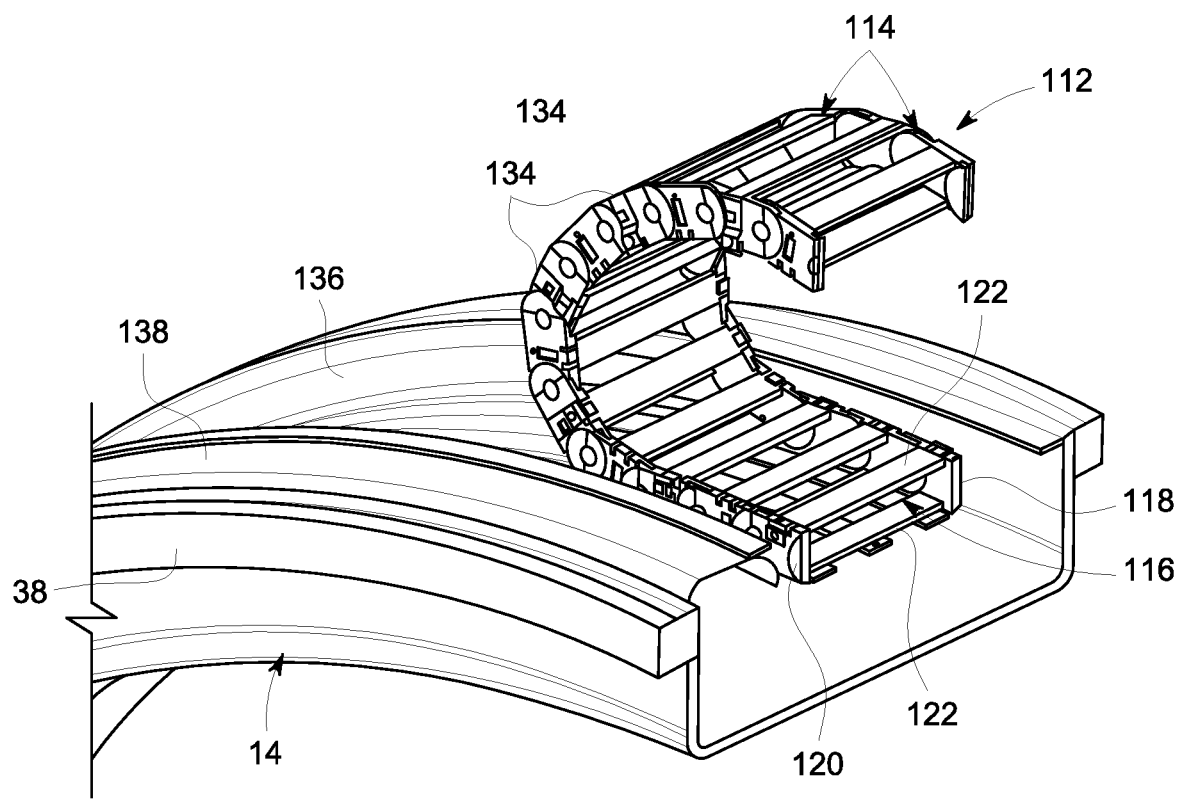
FIG. 7 is a partially broken away isometric view of a cable chain releasably engaged within a channel in the C-arm of the C-arm imaging system of FIG. 6.

With regard now to FIGS. 3-5, in one exemplary embodiment, the housing 102 is formed to extend from each side of the carriage 34 along the shape of the C-arm 14, defining an upper housing 130 and a lower housing 132. In a vertical position for the C-arm imaging system 10 (FIG. 3), the cable chain 112 is oriented within the interior 110 of the housing 102 in an inverted loop 131, with the cable chain 112 initially extending from the end 108 of the housing 102 towards the carriage 34. Adjacent the carriage 34, the cable chain 112 then curves, i.e., curves in an inward and upward direction towards the C-arm 14, and reverses direction to extend along the housing 102 adjacent the C-arm 14 to the connection of the cable chain 112 to the C-arm 14, such that the entire length of the cable chain 112 is retained within the upper housing 130. As the carriage 34 and the C-arm 14 define a space 125 therebetween to allow for free movement of the C-arm 14 relative to the carriage 34, the space 125 allows for the disposition and movement of the cable chain 112 between the C-arm 14 and the carriage 34 without impairing movement of the C-arm 14 with regard to the carriage 34.

In FIG. 4, when the C-arm 14 is moved from the vertical position of FIG. 3 to a horizontal position at one end of the range of motion of the C-arm 14 where the detector 44 is disposed opposite the base 12 and/or carriage 34, the connection point 128 is disposed away from the base 12. As the C-arm 14 moves to this position, the second end 129 of the cable chain 112 secured to the connection point 128 moves along with the C-arm 14 to draw the cable chain 112 out of the upper housing 130. The articulation provided to the cable chain 112 by the pivoting engagement of the sections 114 forming the cable chain 112 allows the cable chain 112 to closely conform to the C-arm 14, and thus not present any obstructions in the area surrounding the C-arm 14.

Looking now at FIG. 5, when the C-arm 14 is moved to the other end of the range of motion of the C-arm 14, i.e., with the X-ray source 46 positioned generally opposite the base 12, the cable chain 12 remains connected to the end 108 of the housing 102. However, in this position of the C-arm 14, the cable chain 112 extends along the interior 110 of both the upper housing 130 and the lower housing 132 within the space 125 between the C-arm 14 and the carriage 34. In this position of the C-arm 14, the cable chain 112 is entirely disposed within the housing 102, such that there are no obstructions formed by the cable chain 112 to interfere with a physician or other equipment positioned and/or moving around the C-arm 14.

Additionally, in another exemplary embodiment of the disclosure illustrated in FIGS. 6-10, to assist in positioning the cable chain 112 in a non-obstructing position when the C-arm 14 is in the position of FIG. 4, the C-arm 14 can include a groove 136 formed in an outer surface 138 of the C-arm 14. The groove 136 is shaped to receive the portions of the cable chain 112 therein when the cable chain 112 is disposed against the outer surface 138 of the C-arm 14, such as shown in FIG. 4. When disposed within the groove 136, the cable chain 112 is retained within the profile of the C-arm 14 such that no part of the cable chain 112 extends outwardly from the C-arm 14 to present any obstruction to physicians and/or equipment in the area surrounding the C-arm 14. Further, the cable chain 112 can be retained within the groove 136 by gravity and/or by the operation of a number of engagement members 134 to be described that are disposed within the groove 136 and operable to engage and disengage the cable chain 112 in correspondence with the movement of the C-arm 14.

In the exemplary embodiment illustrated in FIGS. 6-10, to assist in holding the cable chain 112 in the desired configuration within the housing 102 and/or the groove 136, the housing 102, e.g., the upper housing 130 and/or the lower housing 132, and/or the groove 136 can include a number of engagement members 134 disposed in the interior 110 of the housing 102 and/or within the groove 136. The engagement members 134 operate to selectively engage and hold the cable chain 112 within the housing 102,130,132 until the movement of the C-arm 14, and consequent movement of the cable chain 112 disengages the cable chain 112 from the engagement structures 134. Conversely, any movement of the C-arm 14 that repositions the cable chain 112 within the housing 102,130,132 causes the engagement members 134 to re-engage the cable chain 112 to hold the cable chain 112 in the interior 110 of the housing 102,130,132. With the engagement members 134, the movement of the cable chain 112 corresponding to the movement of the C-arm 14 can effectively be directed along the space 125 to prevent interference of the cable chain 112 with movement of the C-arm 14, in addition to preventing obstructions of the cable chain 112 in the area surrounding the C-arm 14.

The engagement members 134 also operate to engage and hold the cable chain 112 when disposed within the groove 136 and are self-locking to retain the cable chain 112 in the groove 136 without any mechanisms external to the engagement members 134. The engagement members 134 are also operable separately from the operation of the C-arm 14 and imaging system 10. As such, the engagement members 134 will retain the cable chain 112 within the groove 136 even when power is interrupted to the C-arm 14. Also, the engagement members 134 can be disengaged from the cable chain 112 separately from the operation of the C-arm 14.

Figure 8:
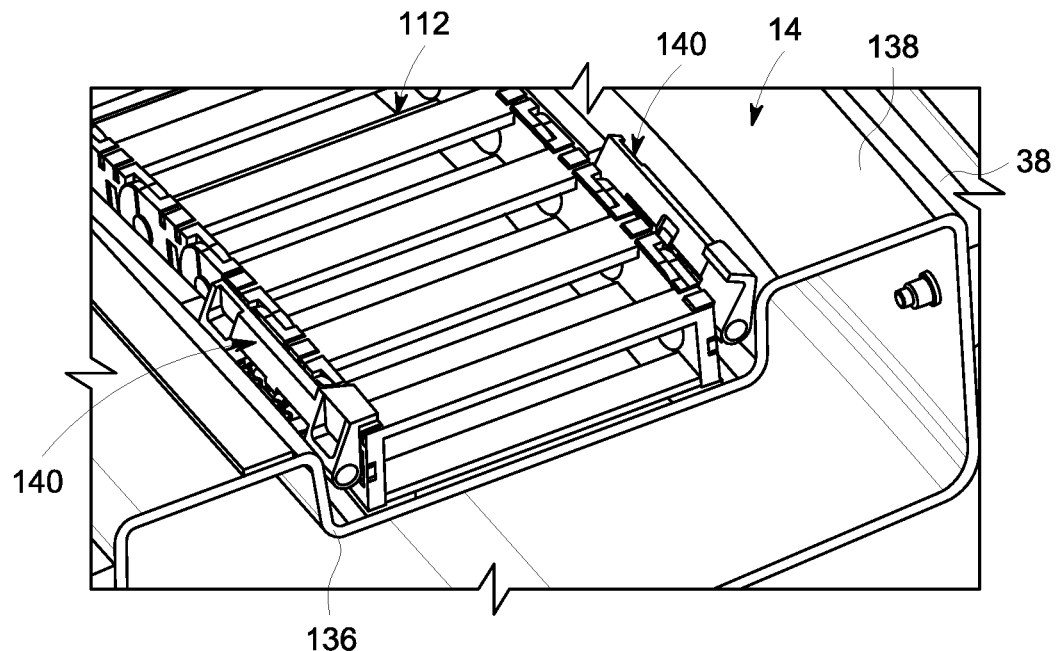
FIG. 8 is a partially broken away isometric view of the cable chain engaged with a clamp disposed within the groove of the C-arm imaging system of FIG. 7 according to an exemplary embodiment of the disclosure.
Figure 9:
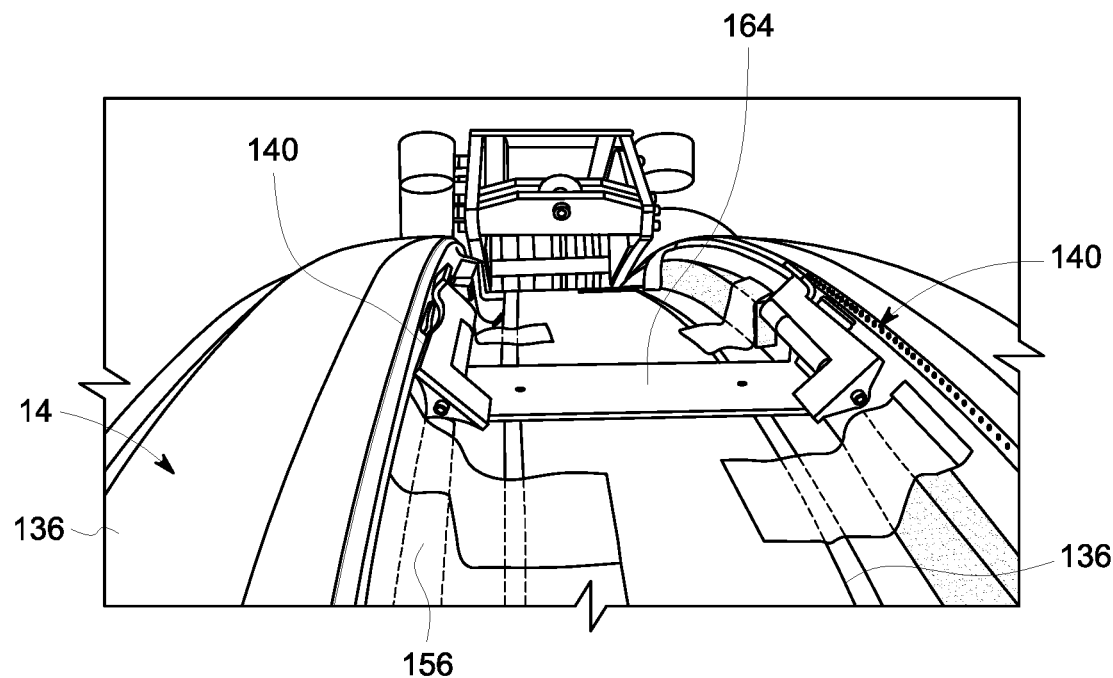
FIG. 9 is a perspective view of the groove of the C-arm of FIG. 8 including hr clamp disposed therein according to an exemplary embodiment of the disclosure.
Figure 10:
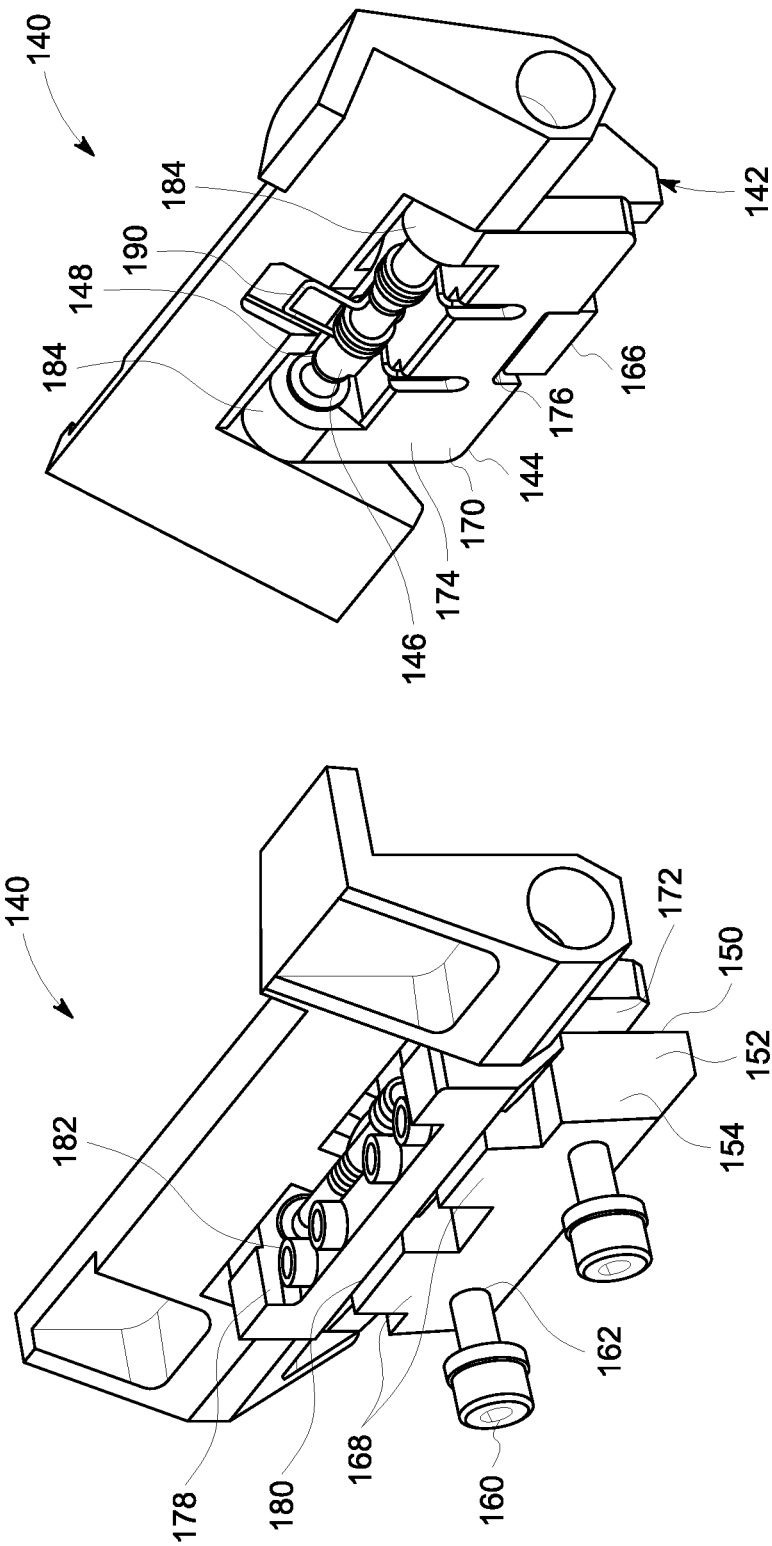
FIG. 10 is an isometric view of the clamp of FIG. 9 according to an exemplary embodiment of the disclosure.

Referring now to FIGS. 8-10, in one exemplary embodiment, the engagement members 134 are each formed with a pair of opposed clamps 140 spaced from one another on opposed sides of the housing 102, or the groove 136 as shown in FIGS. 8-10. The clamps 140, as best shown in FIG. 10, are each formed of a positioning member 142, a pivot arm support 144, which can be formed as part of the positioning member 142, a pivot arm 146, a biasing member 148 and a clamp arm 150.

The positioning member 142 includes a body 152 having a rear surface 154 formed complementary to the shape of the side 156 of the groove 136, and a front mounting surface 158 opposite the rear surface 154. The rear surface 154 is placed against the side 156 (FIG. 9) of the groove 136 and secured thereto using suitable fasteners 160 inserted through aligned apertures (not shown) in the side 156 and bores 162 in the rear surface 154. In an alternative embodiment, an alignment member 164 (FIG. 9) can extend between and connect the front surfaces 158 in order to align the clamps 140 on each side 156 of the groove 136. The body 152 further includes a forward positioning tab 166 extending outwardly from the front surface 158, and a pair of mounting tabs 168 extending upwardly from the body 152 between the rear surface 154 and the front surface 158.

The pivot arm support 144 is formed with a body 170 having a first side 172 formed complementary to the front surface 158 and a flat second side 174 located opposite the first side 172. The body 170 defines a notch 176 at a lower end that receives the forward positioning tab 166 therein to properly seat the support 144 on the positioning member 142. The body 170 also extends over the mounting tabs 168 to align openings 178 in the body 170 with bores 180 in the mounting tabs 168. The openings 178 and bores 180 receive fasteners 182 therein that secure the body 170/pivot arm support 144 to the positioning member 142.

Adjacent the openings 178, the body 170 also includes a pair of upwardly extending tabs 184. The tabs or projections 184 support the pivot arm 146 extending therebetween and upon which is disposed the biasing member 148 between the projections 184. The biasing member 148 in the illustrated exemplary embodiment is formed of a spring 190 having a coil 192 disposed around the pivot arm 146, a brace 194 extending outwardly from the coil 192 and engages within a slot 196 formed in the body 170, and a biasing arm 198 extending outwardly from the coil 192 generally opposite the brace 194. To provide the biasing force, the engagement of the brace 194 with the body 170 provides resistance to the rotation of the coil 194 and biasing arm 198 around the pivot arm 146 with respect to the pivot arm support 144. Thus, any force resulting in movement of the biasing arm 198 against the bias of the brace 194 is opposed by the spring 190.

The pivot arm 146 extends completely through apertures 200 in each of the tabs 184 into engagement within sleeves 202 formed in opposite sides 204,206 of the clamp arm 150. The clamp arm 150 includes a body 208 that extends between the first side 204 and the second side 206 of the clamp arm 150, and includes a slot 210 formed therein. The slot 210 receives the biasing arm 198 such that the bias of the spring 190 operates to rotate the clamp arm 150 in a direction to position the body 208 over the positioning member 142.

The first side 204 of the clamp arm 150 is formed with a landing 212 within which the sleeve 200 is formed and including a planar engagement surface 214. The landing 212 and the engagement surface 214 are formed to be planar with and to extend outwardly from the body 208 to overlap a portion of the positioning member 142 and pivot arm support 144. The bias of the spring 190 pivots the body 208 to a position where the end 216 of the landing 212 opposite the body 208 is angled outwardly in front of the pivot arm support 144.

The second side 206 of the clamp arm 150 also includes a landing 218 incorporating the sleeve 202 therein. Landing 218 also includes a locking member 220 disposed on the landing 218 opposite the sleeve 202 and extending in a direction perpendicular to the engagement surface 214 on the first side 204.

Figure 11:
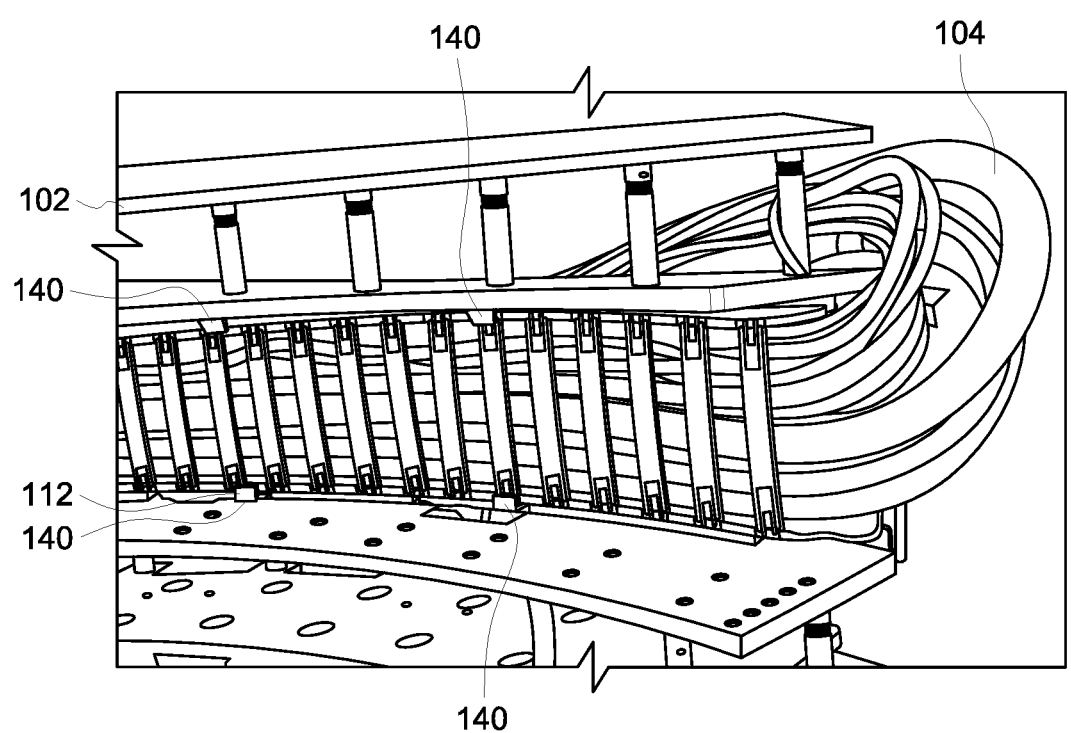
FIG. 11 is a perspective view of the cable chain engaged with a number of clamps within the housing of the x-ray imaging system of FIG. 6.

In operation, prior to engagement with the cable chain 112, the clamps 140 are in the position shown in FIGS. 8 and 9, with the biasing member 148 urging the clamp arm 150 over the positioning member 142 to locate the engagement surface 214 in front of the pivot arm support 144. As the cable chain 112 moves into the groove 136 based on movement of the C-arm 14, the cable chain 112 comes into contact with the engagement surface 214. The force exerted by the cable chain 112 on the engagement surface 214 ultimately exceeds the bias on the clamp arm 150 from the biasing member 148, such that the pressing of the cable chain 112 on the landing 212 and engagement surface 214 ultimately rotates the clamp arm 150 to move the landing 212 downwardly towards the pivot arm support 144. The engagement surfaces 214 on each clamp arm 150 can be coated with a material to reduce wear caused by repeated contact of the cable chain 112 with regard to the engagement surface 214, such as a Teflon® coating material, .Simultaneously, the rotation of the clamp arm 150 causes the locking member 220 to rotate forward with regard to the pivot arm support 144 to locate the locking member 220 directly over the cable chain 112, as best shown in FIGS. 8 and 10. Thus, with the weight and direction of the cable chain 112 positioned against the landing 212, the cable chain 112 activates the clamp 140 to engage and hold the cable chain 112 in position within the groove 136 (FIG. 8) and/or the housing 102 (FIG. 11).

Conversely, when the movement of the C-arm 14 causes the cable chain 112 to move out of and away from the groove 136 and/or the housing 102, as the cable chain 112 initially moves upwardly the force exerted by the cable chain 112 on the landing 212 is lessened, allowing the biasing member 148 to urge and rotate the clamp arm 150 with regard to the pivot arm support 144. The rotation of the clamp arm 150 moves the locking member 220 away from the position over the cable chain 112, allowing the cable chain 112 to be displaced upwardly and outwardly from the groove 136.

In this manner, the clamp 140 operates using only the weight and position of the cable chain 112 in conjunction with the force of the biasing member 148 to engage and disengage the clamp 140 with the cable chain 112. Thus, the clamp 140 is operable separately from the imaging device 10, such that the clamp 140 can hold the cable chain 112 on the housing 102 or C-arm 14 even when power is not provided to the imaging device 10.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A C-arm x-ray imaging device comprising:
   a base;
   a carriage operably connected to the base and having at least one axis of movement with respect to the base
   a C-arm movably connected to the carriage, the C-arm including an x-ray source and an x-ray detector disposed thereon in alignment with one another; and
   a cable management system comprising:
   a housing disposed on the carriage, the housing defining an interior;
   a number of cables extending from the base into the interior of the housing;
   a cable chain having a first end secured within the interior of the housing and a second end affixed to the C-arm, the cable chain defining a channel therein that receives the number of cables to direct the number of cables from the base to the C-arm; and at least one clamp releasably engageable with the cable chain to hold the cable chain in alignment with the at least one of the housing and the C-arm,
wherein the at least one clamp comprises:
a first clamp disposed on one side of the at least one of the housing and the C-arm;
a second clamp disposed on an opposite side of the at least one of the housing and the C-arm; and
an alignment member extending between the first clamp and the second clamp across the at least one of the housing and the C-arm.

2. The C-arm x-ray imaging device of claim 1, wherein the at least one clamp is self-locking.

3. The C-arm x-ray imaging device of claim 1, wherein the at least one clamp is operable separately from the C-arm x-ray imaging device.

4. The C-arm x-ray imaging device of claim 1, wherein the at least one clamp is disposed within the interior of the housing.

5. The C-arm x-ray imaging device of claim 1, wherein the C-arm includes a groove extending along an outer surface of the C-arm capable of receiving a portion of the cable chain therein, and wherein the first clamp, the second clamp and the alignment member are is disposed within the groove.

6. The C-arm x-ray imaging device of claim 5, wherein the clamp comprises:
a positioning member having a rear surface formed complementary to a portion of the C-arm imaging device;
a pivot arm attached to the positioning member;
a biasing member disposed on the pivot arm; and
a clamp arm rotatably mounted to the pivot arm,
wherein the biasing member is engaged between the positioning member and the clamp arm to move the clamp arm between a release position and a locking position.

7. The C-arm x-ray imaging device of claim 6, wherein the biasing member is a spring.

8. The C-arm x-ray imaging device of claim 7, wherein the spring comprises:
a coil disposed around the pivot arm,
a brace extending outwardly from the coil and engaged with the positioning member; and
a biasing arm extending outwardly from the coil and engaged with the clamp arm.

9. The C-arm x-ray imaging device of claim 7, wherein the clamp arm includes a first end having an engagement surface thereon and a second end including a locking member thereon, wherein the locking member is disposed on the second end perpendicularly relative to the engagement surface.

10. A clamp for releasably engaging a cable chain employed on a C-arm X-ray imaging device, the clamp comprising:
a positioning member having a rear surface formed complementary to a portion of the C-arm imaging device;
a pivot arm attached to the positioning member;
a biasing member disposed on the pivot arm; and
a clamp arm rotatably mounted to the pivot arm,
wherein the biasing member is engaged between the positioning member and the clamp arm to move the clamp arm between a release position and a locking position.

11. The clamp of claim 10, wherein the clamp arm includes a first end having an engagement surface thereon and a second end including a locking member thereon, wherein the locking member is disposed on the second end perpendicularly relative to the engagement surface.

12. The clamp of claim 10, wherein the pivot arm extends outwardly from opposed sides of the positioning member into engagement with the first end and the second end of the clamp arm.

13. The clamp of claim 10, further comprising:
a first clamp;
a second clamp; and
an alignment member extending between the first clamp and the second clamp.

14. The clamp of claim 10, wherein the biasing member is a spring.

15. The clamp of claim 14, wherein spring comprises:
a coil disposed around the pivot arm,
a brace extending outwardly from the coil and engaged with the positioning member; and
a biasing arm extending outwardly from the coil and engaged with the clamp arm.

16. A method of managing the position of cables connecting a detector and an x-ray source of a C-arm to a base of a C-arm x-ray imaging device, the method comprising the steps of:
providing a C-arm-ray imaging device comprising:
a base;
a carriage operably connected to the base and having at least one axis of movement with respect to the base;
a C-arm movably connected to the carriage, the C-arm including an x-ray source and an x-ray detector disposed thereon in alignment with one another; and
a cable management system comprising:
a housing disposed on the carriage, the housing defining an interior;
a number of cables extending from the base into the interior of the housing;
a cable chain having a first end secured within the interior of the housing and a second end affixed to the C-arm, the cable chain defining a channel therein that receives the number of cables to direct the number of cables from the base to the C-arm; and
at least one clamp releasably engageable with the cable chain to hold the cable chain in alignment with the at least one of the housing and the C-arm;
placing the number of cables within the cable chain; and
moving the C-arm relative to the carriage; and
engaging the cable chain with the at least one clamp to maintain the cable chain within a profile of at least one of the housing or the C-arm,
wherein the step of engaging the cable chain with the at least one clamp comprises:
contacting a clamp arm on the at least one clamp with the cable chain; and
pivoting a locking member disposed on the clamp arm over the cable chain.

17. The method of claim 16, wherein the C-arm includes a groove formed in an outer surface of the C-arm, and wherein at least one clamp is disposed within the groove, and wherein the step of engaging the cable chain with the at least one clamp comprises positioning the cable chain within the groove to engage the at least one clamp.

18. The method of 16, wherein the clamp arm is a spring-biased clamp arm and wherein the step of pivoting the locking member over the cable chain comprises contacting the clamp arm with the cable chain to overcome the bias of the spring biased clamp arm.

\* \* \* \* \*